(12) United States Patent
Yagi

(10) Patent No.: US 6,400,795 B2
(45) Date of Patent: Jun. 4, 2002

(54) X-RAY FLUORESCENCE ANALYZER

(75) Inventor: Shigeki Yagi, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/910,107

(22) Filed: Jul. 20, 2001

(30) Foreign Application Priority Data

Jul. 27, 2000 (JP) ...................................... 2000-227376

(51) Int. Cl.[7] ......................................... G01N 23/223
(52) U.S. Cl. ....................................................... 378/45
(58) Field of Search ................................. 378/44–50

(56) References Cited

U.S. PATENT DOCUMENTS 4,954,714 A * 9/1990 Pollak et al. ................. 378/45

* cited by examiner

*Primary Examiner*—Craig E. Church
(74) *Attorney, Agent, or Firm*—Adams & Wilks

(57) ABSTRACT

An X-ray fluorescence analyzer utilizing principles of an X-ray fluorescence method comprising X-ray generation means 1 for generation of X-rays, a shutter 2 for shielding against X-ray beam irradiation, generated by the X-ray generation means, to a sample to be measured, X-ray detection means 4 for detecting secondary X-rays, generated as the result of X-ray beam irradiation, to a sample to be measured, measurement control instruction means 5 for instructing to start and to stop measurement, operation delay means 6 for outputting a signal to shutter actuating means 3 after a fixed period of time has elapsed after the measurement start instruction signal from the measurement control instruction means 5 is input, and display means 7 for displaying that the X-ray fluorescence analyzer is performing measurement during the period when from the measurement start instruction signal is input from the measurement control instruction means 5 until the measurement stop instruction signal is input.

2 Claims, 2 Drawing Sheets

X-RAY FLUORESCENCE ANALYZER

BACKGROUND OF THE INVENTION

The present invention relates to an X-ray fluorescence analyzer mainly aimed at outdoor elementary analysis, such as archaeological sample examination, criminal field searches, fire patrol searches, and scrap article inspection, etc.

1. Related Art

Archaeological sample examination, criminal field searches, fire patrol searches, and scrap article inspection etc., are often performed outside.

Also, criminal field searches and fire patrol searches are carried out day and night regardless of the time. There are cases where other operations are carried out while the elementary analysis is being performed and operators are often forced to carry out analysis under bad conditions, such as with noise or under bad visibility.

In the case of a portable X-ray fluorescence analyzer comprising a measurement head and a host, in order to make ordinary operations efficient there are two operators, one for arranging the measurement head facing towards a sample, and another operating the host of the analyzer to collect measurement data, and the two operators cooperate with each other to perform measurement.

When arranging the measurement head facing towards a sample, as disclosed in Japanese Patent laid open No. Hei. 11-304733, a microswitch for operating a safety interlock is turned on to performed positional alignment.

Next, an operator on the measurement head side notifies the completion of the arrangement of the measurement head to an operator on the host side. The operator on the host side then notifies the start of the measurement, and actually operates to start measurement.

When measurement of one sample is completed, the operator on the host side notifies the completion of measurement to the operator on the measurement head side.

Upon receiving the sign, the operator on the measurement head side starts arrangement for the next sample measurement. These communications are repeated during the operation.

X-rays cannot be measured with the naked eye, and whether or not X-rays are actually irradiated from the measurement head can only be determined according to the information from the operator on the host side, who is issuing the start and stop measurement instructions.

The safety of the operator on the head side is maintained by a safety interlock structure, utilizing the microswitch mounted on the measurement head housing.

Namely, hardware functions not to irradiate X-rays externally as long as the position adjustment, for turning the microswitch on, of the measurement head and the sample is not carried out. Therefore the operator on the measurement head side can maintain safety by themselves.

The difficulty of the position adjustment of the measurement head and the sample differs depending on the shape, state, fixed position, etc. of the sample. Accordingly, the period of time required for the position adjustment varies according to the case.

Under these circumstances, it is necessary for the operator on the measurement head side and the operator on the host side to call out to each other or exchange some kind of signs to cooperate with each other well. However, a portable X-ray fluorescence analyzer is often used under bad conditions, such as in a noisy environment or under bad visibility. In this case, the operators cannot exchange words or signs smoothly, and working efficiency decreases.

SUMMARY OF THE INVENTION

The present invention has as its object to provide a portable X-ray fluorescence analyzer having high working efficiency, to solve the above described problems.

To resolve the above problems, the portable X-Ray fluorescence analyzer of the present invention comprises drive delay means for outputting a signal to shutter driving means 3 after a fixed period of time has elapsed after the measurement start instruction signal from the measurement control instruction means 5 is input, and display means for displaying that the X-ray fluorescence analyzer is performing measurement during the period from when the measurement start instruction signal is input from the measurement control instruction means until the measurement stop instruction signal is input.

Also, the portable X-ray fluorescence analyzer, utilizing principles of an X-ray fluorescence method, is made up of an X-ray tube applied with high voltage for generating X-rays, a shutter for shielding against X-ray beam generated by the X-ray tube and irradiated to a sample to be measured, a solenoid for opening and closing the shutter, a semiconductor detector (SSD) for detecting secondary X-rays, generated as a result of x-ray beam irradiation to the sample to be measured, a measurement start/stop switch or a measurement control program for instructing start and stop of measurement, a signal delay circuit for outputting a signal to the solenoid after a fixed period of time has elapsed after the measurement start instruction signal from the measurement start/stop switch or the measurement control program is input, an LED or a lamp for displaying that the X-ray fluorescence analyzer is performing measurement during the period from when the measurement start instruction signal is input from the measurement start/stop switch or the measurement control program, until the measurement stop instruction signal is input, and display means such as a monitor of the personal computer.

When the operator on the host side instructs start of measurement, the display means immediately displays that the X-ray fluorescence analyzer is performing measurement, and after a delay of a fixed period of time, a shutter opens.

Namely, the operator on the measurement head side can have a delay for the fixed period of time, from recognizing measurement start, until primary X-rays are irradiated outward from the analyzer.

Also, when the operator on the host side instructs to stop measurement, the display means immediately displays that the X-ray fluorescence analyzer has stopped measurement, and the shutter is closed at the same time to stop outward irradiation of X-rays.

DETAILED DESCRIPTION OF THE PREFERRED EMBODIMENT

An embodiment of the present invention will be described in the following based on the drawings.

Figure 1:
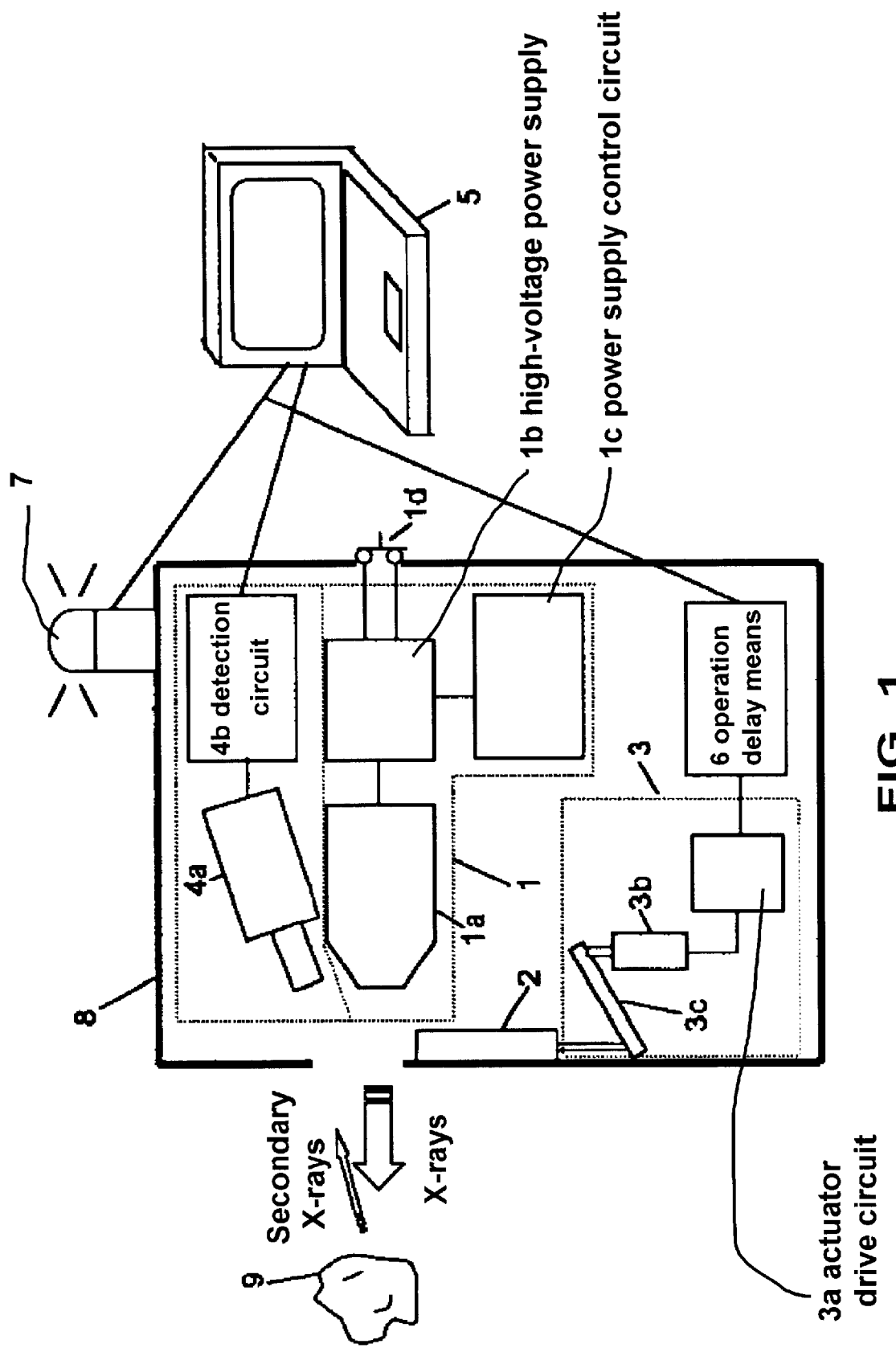
FIG. 1 is diagram showing the structure of the X-ray fluorescence analyzer of the present invention.

FIG. 1 is a view showing a configuration for the present invention. A shutter 2 in FIG. 1 is made of metal of a sufficient thickness to be able to completely shield against X-ray. X-ray generation means 1 comprises an x-ray tube 1a, a high-voltage power supply 1b, a power supply control circuit 1c, and an X-ray on/off switch 1b, X-ray generation means 1a is realized as a small lightweight device by adopting an end window type small x-ray tube.

X-ray fluorescence beam, generated from the X-ray generation means 1, passes through a reorganization solace provided in a measurement head housing 8 of the X-ray fluorescence analyzer, and is irradiated onto a sample to be measured 9. However, while measurement is not in progress, the X-ray are shielded by the shutter 2 and there is no leakage of X-ray outward from the measurement head. The shutter 2 is operated to open and to closed by action of the action of the actuator such as a solenoid. The drive of the actuator is controlled by electrical signals. Having the electrical signals as input, the block, comprising the actuator drive circuit 3a, actuator 3b, and power transmission structure 3c, constitutes the shutter drive means 3. The X-ray detector 4a and the detection circuit 4b constitute the X-ray detection means 4. The output signal from the detection circuit 4b is taken into a computer, and various kinds of data analysis are then carried out. The computer controls not only the data analysis but also the whole system of the X-ray fluorescence analyzer. The instructions for starting or stopping measurement are also sent from the computer. Therefore, in this embodiment, the measurement control instruction means 5 are realized by adopting a computer.

The measurement control instruction means 5 sends a signal to the measurement head, and instructs to start measurement. The signal is sent to the display means 7, and at the same time, to the operation delay means 6.

Receiving the signal, the display means 7 shows that the X-ray fluorescence analyzer system is performing measurement. Specifically, it visually attracts the attention of the operator on the measurement head side or other people around, such as by illuminating a red lamp.

Meanwhile, the operation delay means 6, also receiving the signal from the measurement control instruction means 5, sends out a measurement start instruction signal to the shutter drive means 3 after the fixed period of time has elapsed after receiving the measurement start instruction signal. Receiving the measurement start instruction signal from the operation delay means 6, the shutter drive means 3 drives the shutter 2 to open. Accordingly, when the operator on the host side instructs start of measurement, the display means immediately shows that the X-ray fluorescence analyzer is performing measurement, and the shutter 2 opens after as delay of a fixed period of time. Therefore a safety margin of a fixed period of time can be obtained after the measurement start instruction until primary X-rays are irradiated outward from the analyzer.

Figure 2:
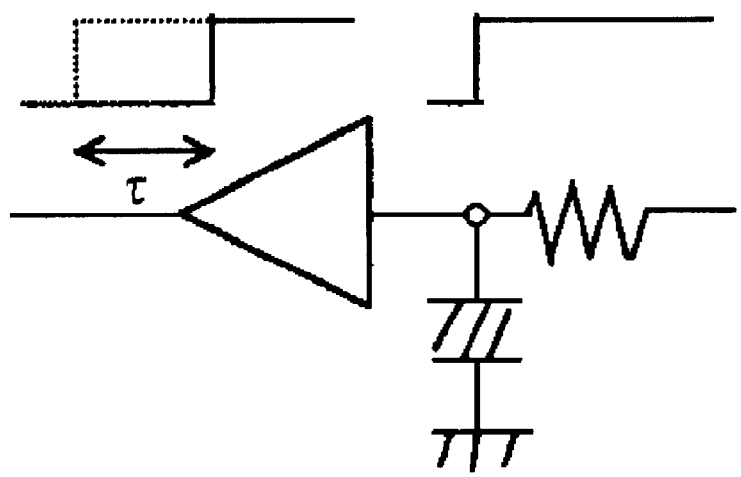
FIG. 2 is a diagram showing one example of the structure of the operation delay means of the embodiment of the present invention.
Figure 3:
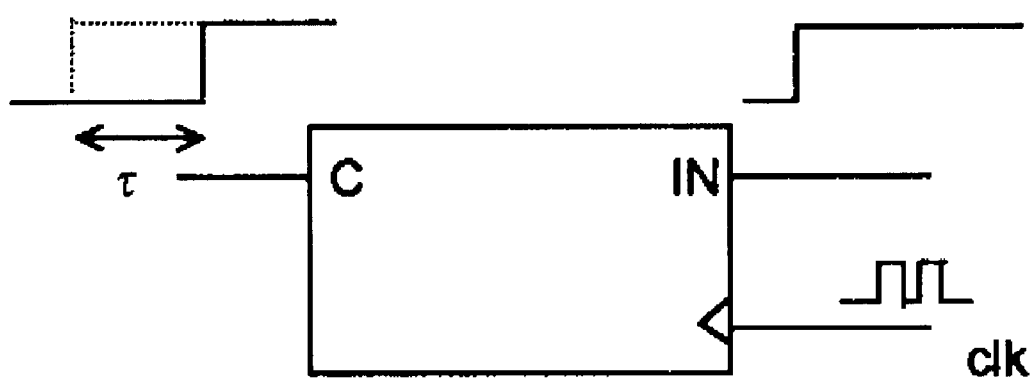
FIG. 3 is a diagram showing an example of the structure of the operation delay means of the embodiment of the present invention.

Normally several seconds are enough for this delay time, and the operation delay means 6 can be implemented with, for example, a CR delay circuit shown in FIG. 2, or a simple timer circuit shown in FIG. 3. Upon receipt of a measurement stop instruction from the measurement control instruction means 5, the display means 7 stops displaying that the system is performing measurement. At the same time, the operation delay means 6 immediately transmits a measurement stop instruction to the shutter drive means 3, and the shutter 2 is then closed. An X-Ray Fluorescence Analyzer comprises an operation delay means for outputting a signal to a shutter drive means after a fixed period of time has elapsed after a measurement start instruction signal is input from the measurement control instruction means, and a display means for displaying that the X-ray fluorescence analyzer is performing measurement after a measurement start instruction signal is input until a measurement stop signal is input from the measurement control instruction means. When the operator on the host side instructs to start measurement, the display means immediately displays that the X-ray fluorescence analyzer is performing measurement. Accordingly the shutter opens after a delay of a fixed period of time, and a delay can be obtained for a fixed period of time from a measurement start instruction until the actual irradiation of Primary X-rays outward from the analyzer.

Accordingly, the operator on the measurement head side can determine the actual timing of measurement start from the display contents at the display means.

As shown in the embodiment, if a red lamp is used for the display means, reliable information transmission of measurement start or stop can be achieved during the operation, even at night or in noisy conditions. The timing of the measurement start or stop can be determined reliably, which means that the term of the X-ray being irradiated outward can also be determined precisely. Namely, the operators can precisely determine the timing while protecting against exposure to the X-rays.

Moreover, the operator on the measurement head side can also prevent accidents in case where the operator on the host side has instructed to start measurement in spite of not adequately preparing from a safety standpoint, according to his own decision by turning off the X-ray on/off switch during the delay.

Accordingly, safety can be achieved without relying on the safety interlock means with a microswitch. Therefore the limiting conditions regarding the measurement head arrangement decrease, and the operation efficiency is improved. As a result, a plurality of samples can be measured at certain intervals.

What is claimed is:

1. An X-ray fluorescence analyzer, utilizing principles of an X-ray fluorescence method, comprising:

X-ray generation means for generating X-rays;

a shutter for shielding against X-ray beam generated from the X-ray generation means and irradiated to a sample to be measured;

shutter drive means for opening and closing the shutter;

X-ray detection means for detecting secondary X-rays, generated as the result of X-ray beam irradiation, to a sample to be measured;

measurement control instruction means for instructing start and stop of measurement;

operation delay means for outputting a signal to the shutter drive means after a fixed period of time has elapsed after the measurement start instruction signal from the measurement control instruction means is input; and display means for displaying that the X-ray fluorescence analyzer is performing measurement during the period from the measurement start instruction signal is inputted from the measurement control instruction means until the measurement stop instruction signal is inputted.

2. An X-ray fluorescence analyzer, utilizing principles of an X-ray fluorescence method, comprising:

an X-ray tube applied with high voltage for generating X-rays;

a shutter for shielding against X-ray beam generated from the X-ray tube and irradiated to a sample to be measured;

a solenoid for opening and closing the shutter;

a semiconductor detector for detecting secondary X-rays generated as a result of X-ray beam irradiation to the sample to be measured;

a measurement start/stop switch or a measurement control program for instructing start and stop measurement;

a signal delay circuit for outputting a signal to the solenoid after a fixed period of time has elapsed after a measurement start instruction signal from the measurement start/stop switch or the measurement control program is input;

an LED or a lamp for indicating that the X-ray fluorescence analyzer is performing measurement during the period from when the measurement start instruction signal is input from the measurement control instruction means until the measurement stop instruction signal is input; and display means such as a personal computer monitor.

* * * * *